(12) United States Patent
Mohr et al.

(10) Patent No.: US 9,096,824 B2
(45) Date of Patent: Aug. 4, 2015

(54) CULTURE/EXPOSURE DEVICE, IN PARTICULAR FOR CELL AND/OR BACTERIA CULTURES

(76) Inventors: Ulrich Mohr, Hannover (DE); Michaela Aufderheide, Hannover (DE); Beat Halter, Herisau (CH)

(*) Notice: Subject to any disclaimer, the term of this patent is extended or adjusted under 35 U.S.C. 154(b) by 838 days.

(21) Appl. No.: 13/122,672

(22) PCT Filed: Oct. 1, 2009

(86) PCT No.: PCT/EP2009/007054
§ 371 (c)(1),
(2), (4) Date: May 4, 2011

(87) PCT Pub. No.: WO2010/040473
PCT Pub. Date: Apr. 15, 2010

(65) Prior Publication Data
US 2011/0212515 A1    Sep. 1, 2011

(30) Foreign Application Priority Data

| Oct. 6, 2008 | (DE) | 10 2008 050 076 |
|---|---|---|
| Oct. 6, 2008 | (DE) | 10 2008 050 077 |
| Oct. 6, 2008 | (DE) | 10 2008 050 079 |
| Oct. 6, 2008 | (DE) | 10 2008 050 080 |
| Nov. 11, 2008 | (DE) | 10 2008 056 684 |
| Nov. 11, 2008 | (DE) | 10 2008 056 685 |
| Nov. 11, 2008 | (DE) | 10 2008 056 686 |
| Nov. 11, 2008 | (DE) | 10 2008 056 763 |
| Apr. 7, 2009 | (DE) | 10 2009 016 364 |

(51) Int. Cl.
*C12M 1/34* (2006.01)
*C12M 3/00* (2006.01)
(Continued)

(52) U.S. Cl.
CPC ............ *C12M 41/46* (2013.01); *C12M 23/00* (2013.01); *C12M 23/44* (2013.01); *C12M 29/26* (2013.01);
(Continued)

(58) Field of Classification Search
CPC ...... C12M 23/44; C12M 29/00; C12M 29/26; C12M 41/46; G01N 33/5008; G01N 1/2208; G01N 1/2273; G01N 2001/2223
USPC .................. 435/287.1, 287.3; 73/863.22
See application file for complete search history.

(56) References Cited

U.S. PATENT DOCUMENTS

| 2004/0168694 A1 | 9/2004 | Fukano et al. |
| 2005/0170499 A1 | 8/2005 | Mohr et al. |

(Continued)

FOREIGN PATENT DOCUMENTS

| DE | 19526533 | 1/1997 |
| DE | 10014057 | 10/2001 |

(Continued)

OTHER PUBLICATIONS

Savi et al. "A Novel Exposure System for the Efficient and Controlled Deposition of Aerosol Particles onto Cell Cultures." Environ. Sci. Technol. (2008), vol. 42, pp. 5667-5674.*

(Continued)

*Primary Examiner* — William H Beisner
(74) *Attorney, Agent, or Firm* — Bachman & LaPointe, P.C.

(57) ABSTRACT

In a culture/exposure device, in particular for cell and/or bacteria cultures, having receptacles (10, 12, 14) for culture containers (11, 13, 15) in a base body (4) and having a flow guide, which has an inlet (20), for supplying a test atmosphere to the culture container (11, 13, 15), it is provided that the device is constructed from a plurality of modules (6, 8, 16, 18, 36) and that the modules be connected to one another so as to be easily releasable from one another.

12 Claims, 10 Drawing Sheets

(51) Int. Cl.
   *G01N 1/22* (2006.01)
   *C12M 1/00* (2006.01)
(52) U.S. Cl.
   CPC .............. *C12M 23/40* (2013.01); *G01N 1/2208* (2013.01); *G01N 1/2273* (2013.01); *G01N 2001/2223* (2013.01)

(56) References Cited

U.S. PATENT DOCUMENTS

2006/0024822 A1  2/2006  Chang et al.
2010/0273246 A1  10/2010  Fukano et al.

FOREIGN PATENT DOCUMENTS

| | | |
|---|---|---|
| DE | 10211324 | 10/2003 |
| EP | 1049765 | 11/2000 |
| EP | 1174496 | 1/2002 |
| EP | 1431746 | 6/2004 |
| WO | 2007/085621 | 8/2007 |

OTHER PUBLICATIONS

English language machine translation of DE10014057 (Oct. 4, 20010), 14 pages.*

* cited by examiner

CULTURE/EXPOSURE DEVICE, IN PARTICULAR FOR CELL AND/OR BACTERIA CULTURES

BACKGROUND OF THE INVENTION

The invention refers to a culture/exposure device and, more particularly, a culture/exposure device for cell and/or bacteria cultures.

Culture/Exposure devices of such kind are generally known and serve, for example, to supplying a test atmosphere to a cell culture and to cultivate the latter in order to determine what effects the test atmosphere has on the cell culture. In particular it is possible to examine what effects for example gases, aerosols, and/or agents in particle form have on cell and bacteria cultures.

Culture/exposure devices of the said kind are known from the EP 1 049 765 B1 and the DE 102 11 324 A1. They have at least two receptacles for cultural containers and a flow guide to supply the cultural container with a test atmosphere. Departing from the flow guide, flow passages extend to the cultural containers, through which flow passages the test atmosphere is led to the cell cultures contained in the cultural containers. After the test atmosphere has been supplied to the cell cultures, the latter are cultivated, removed after the finish of the cultivation and examined. Thus it is possible to reach conclusions as to if and in what respect the test atmosphere takes effects on the cultures.

The object of the invention is to provide a culture/exposure device for cell and/or bacteria cultures, in which the precision and the reproducibility respectively of the study results are improved and the examination possibilities are more varied.

SUMMARY OF THE INVENTION

The object is achieved by the present invention.

An initial basic idea of the invention presented herein is given by structuring the whole device in a modular manner, thus making it easy to operate and easy to disassemble. The individual modules are designed in such a manner that they can also be replaced by other modules. However, a further consideration is to design the modules in such a manner that intra-modular replacement is possible, meaning that essential elements of the individual modules are replaceable through other sub-modules again. Thus a device is created which is very flexible in its usage.

One idea of the invention lies in the fact that the examination possibilities with respect to cell and/or bacteria cultures—hereinafter in brief referred to as cultures—can be enhanced by subjecting the test atmosphere, which is supplied to the cultures, to pretreatment corresponding to the requirements pertaining in each case. To achieve this objective, the invention makes provision for forming the inlet on a preparatory module which is detachably connected with the base body. So, in accordance with the invention, the preparatory module is formed to be replaceable, thus making it possible to use a preparatory module suitable for the respective desired examination.

For example and in particular, it is possible to use a preparatory module in which a pretreatment of the test atmosphere does not take place; rather, the test atmosphere is lead from the inlet through to the cultural container.

When on the other hand, one desires a high as possible fall out of the particles contained in the test atmosphere on to the cultures, then it is suitable to electrostatically charge the particles using a preparatory module, before they are led to the cultural container. In this case, for example, the preparatory module which does not include a pretreatment of the test atmosphere can be replaced by one that includes electrostatic charging.

So, in accordance with the invention the examination possibilities with respect to cell and/or bacteria cultures are substantially broadened.

An even more advanced development of the invention provides toolless detachable connecting means for connecting the preparatory module with the base body. In this embodiment, the preparatory module is toolless replaceable, so that the replacement proceeds especially quick and easy.

A suitable further advanced development of the above defined embodiment provides for the connecting means to produce a tight fit between the preparatory module and the base body. In this manner the preparatory module is securely held on the base body.

An advancement of the embodiment with the preparatory module provides for a base body being detachably connected to a base module for applying an electrostatic field to the cultural container.

A further part of the invention solves the underlying object in that the base body consist of an aerosol guiding module and a sample receptacle module and that the aerosol guiding module and the sample receptacle module are guided relative to each other on a guide and are movable relative to each other through to a drive means between a closed position, in which the flow guide is flow technically connected with the cultural container, and an open position, in which the flow guide is flow technically separated from the cultural container.

One has thus achieved that the fluidic separation of the aerosol guiding module from the sample receptacle module can be easily ensured, thus in addition, making the culture/exposition device securely to operate. A further achievement lies in the fact that time required for the fluidic separation of aerosol guiding module and sample receptacle module is shortened since the invention abstains from additional locking modules, such as screws, clamps and the like, to fixate the closed position.

Additionally, the fluidic connection of aerosol guiding module and sample receptacle module is made more precise by the manner in which the aerosol guiding module and the sample receptacle module are guided.

The relative movement of the aerosol guidance module and the sample receptacle module to another can occur in different manners. In accordance with the invention it is possible, to this end, to move both the aerosol guidance module and the sample receptacle module either simultaneously or one after the other. An addition it is also possible to move only the aerosol guidance module in relation to the sample receptacle module, the latter at the same time remaining movable. In further addition, a reversed movement sequence is also possible, so that the sample receptacle module is moved, while the aerosol guiding module remains static.

A further advancement of the invention consists in the drive means being manually operable. This results in the advantage of a cost effective implementation and use of the culture/exposure device. What is more, the latter thus becomes independent of energy, in particular electrical power.

In accordance with another advancement of the invention the guide has at least one initial linear guide for linear guiding of the aerosol guiding module and the sample receptacle module relative to another between the closed position and the open position. Thus a precise, quick and secure bringing together of aerosol guiding module and sample receptacle module is achieved.

In addition, another advancement of the invention is characterized in that the initial linear guide for creating an automatic, or at least almost automatic movement of the aerosol guiding module towards the open position or towards the closed position has at least one spring, in particular a spiral spring. The spring is tensioned in one direction of movement, by which configuration it can release the stored energy as kinetic energy in the opposite direction.

Thus it is possible to suspend the spring, for example, in one movement aimed at achieving the closed position in order to use the stored energy for an automatic achievement of the open position. Whether the spring is conceived as a tension spring or a pressure spring in this instance depends on the structural positioning of the spring as well as on which direction of movement is to be supported. For this reason it is possible to use the support provided by the spring for a movement aimed at reaching the open position or also the closed position This support is feasible for the movement of the aerosol guiding module as well as for the sample receptacle module by correlating at least one spring to conform with the aerosol guiding module, respectively the sample receptacle module. The spring not only makes it possible to support a movement direction of the aerosol guiding module and/or the sample receptacle module, but also to utilize for example cords which can be held under tension by the spring.

In addition the advancement of the invention provides for the drive means to have at least one gear box to transform an initial movement into a drive movement aimed at moving the aerosol guiding module in relation to the sample receptacle module and/or to transform an initial movement into a drive movement for relatively moving the sample receptacle module to the aerosol guiding module. This results in the forces required to create the relative movement of the aerosol guiding module to the sample receptacle module, respectively, of the sample receptacle module to the aerosol guiding module being smaller.

A further advancement of the invention is defined in that the gear box has at least one cord-, strip-, or chain-shaped traction means aimed at transmitting the initial movement as a drive movement aimed at relatively moving the aerosol guiding module to the sample receptacle module and/or for the relative movement of the sample receptacle module to the aerosol guiding module. This results in the inert masses of the gear box, when set in motion, being kept low, thus enhancing the efficiency of the gearbox. In addition, it is thus possible to design the reception of the initial movement as well as the release of the drive movement to be flexible in their position in space, thus achieving cost advantages.

In addition, another advancement of the invention consists in the gear box transforming the initial movement into a downward movement of the aerosol guiding module towards the sample receptacle module, which movement in particular takes the form of a vertical, or at least mainly vertical, downward movement.

In addition, one of the advancements of the invention is characterized in that the drive means has at least one actuating means aimed at creating an initial movement. The actuating means serves to initiate the movement of the aerosol guiding module, respectively, of the sample receptacle module. As an actuating means, various means may be employed, which may be operated electrically, hydraulically or pneumatically. In addition, manually operable actuating means, which can be a rotary crank or a lever mechanism, are especially preferred in the medical field, in order to meet the high hygienic standards demanded in that field in as simple and cost effective a way as possible.

In addition, an advancement of the invention provides for the guide having a second linear guide for the linear guiding of the sample receptacle module in a direction that is orthogonal, or at least mainly orthogonal, to the guide direction of the first linear guide, in particular to the horizontal or at least mainly horizontal guiding of the sample receptacle module. A second linear guide causes a simpler handling of the culture/exposure device, since the aerosol guiding module and the sample receptacle module can more easily be positioned in relation to each other. In this manner, for example, a replacement of the cultural container, or the cultural containers becomes possible in shorter time intervals.

A further idea of the invention presented herein refers to the fact that the flow guide has a distribution opening or a distribution chamber, from which flow passages lead in essentially the same length towards the individual cultural containers. Correspondingly it is made sure that sub-flows of the test atmosphere, which are led to the individual cultural containers, travel a flow path of essentially the same length between the distribution opening, or distribution chamber, and the respective cultural container. Thus it has been prevented that the contents of the test atmosphere, say smoke, is changed in changing degrees due to flow paths of different lengths leading to the individual cultural containers, which would give adulterated study results.

Thus, the invention, with simple means, makes available a culture/exposure device with improved precision and reproducibility of study results respectively.

As far as the test atmosphere is concerned, in accordance with the invention, this may be, in particular, a gaseous medium, which carries particles, for example an aerosol. However, in accordance with the invention, other test atmospheres may also be utilized.

An advancement of the invention provides for the receptacles for the cultural containers being arranged along the circumference of a circle, preferably in particular equidistant in the direction of the circumference. In this embodiment the design of flow passages having essentially the same length is simplified.

An advancement of the embodiment defined in the immediate above provides for the longitudinal axis of the end on the output side of the flow guide substantially coinciding with the center of the circle.

In accordance with another advancement of the invention, the flow passages run from the longitudinal axis of the end on the output side of the flow guide in a tilted manner towards the cultural containers. In this embodiment, the result is an especially simple and compact structure of the culture/exposure device, in the following also simply referred to as the device.

The flow passages may be formed in any suitable manner, for example by hoses or pipes. In order to give the device in accordance with the invention an especially compact and resistant structure, another advancement of the invention provides for the base body having a flow passage block, in which the distribution opening or the distribution chamber and the flow passages are formed.

An extraordinarily advantageous advancement of the invention provides for the longitudinal axis of the distribution opening or distribution chamber respectively, forming an angle with the longitudinal axis of the respective flow passage, which angle is smaller, preferably substantially smaller than 90°. This results in an especially unimpeded flow process. It is also prevented that particles contained in the test atmosphere excessively deposit at the corners of the flow guide.

Underlying the invention is the further idea to improve the study results obtained while using the culture/exposure device in accordance with the invention by improving the tempering of the cultural container. To this end, the invention provides for the receptacle in the flow path being arranged in such a manner that the cultural container constitutes a barrier for the temper fluid. The fact that the cultural container forms a barrier for the temper fluid results in the cultural container intensively being encompassed by the flow and thus evenly tempered. By choosing the temperature of the temper fluid correspondingly, the cultural container, and consequently a culture contained therein, can be tempered in an especially precise manner, in order to avoid for example condensation. By arranging the receptacle inside the flow path of the temper fluid, hydrodynamic short circuits of the temper fluid between in- and outlet are avoided.

In accordance with the invention, the chamber has a substantially circular limited inner wall. In this manner, especially advantageous flow conditions of the temper fluid result, which in turn ensure an especially even tempering of the cultural container or the cultural containers.

In order to further improve the flow conditions of the temper fluid, another advancement of the invention provides for the receptacle to have a substantially circular limited outer wall. With this embodiment cultural containers with circular limited outer wall can be used, so that especially favorable flow conditions appear.

Other preferable advancements of the invention provide for at least two inlets and/or at least two outlets. If in these embodiments the temper fluid flows through the chamber, at least two flow paths are formed between the inlet or inlets and the outlet or outlets, in which flow paths there is respectively arranged a receptacle for a cultural container, in such a manner that each of the cultural containers allows for a flow barrier for the temper fluid.

The embodiment mentioned in the immediate above is advantageous especially in cases where at least two receptacles for cultural containers are provided, as is the case in a further advancement of the invention.

An advantageous advancement of the pre-mentioned embodiment makes the provision that the receptacles are arranged along the circumference of a circle, which circle is preferably concentric in relation to the inner wall of the chamber.

On principle, a gaseous fluid may be employed as a temper fluid. In order to allow for a simple and precise tempering, another advantageous advancement provides for the temper fluid being a temper liquid.

BRIEF DESCRIPTION OF THE DRAWINGS

In the following, the invention is described in greater detail with reference to the appended drawing, which illustrates embodiments of devices in accordance with the invention. Herein all the features claimed and described in the patent claims and illustrated in the drawing constitute, each one for itself and in any combination amongst each other, the subject of the invention, irrespective of their summarizing in the patent claims and their back reference, as well as irrespective of their description, or illustration in the drawing.

Shown are in.

DETAILED DESCRIPTION

Figure 1:
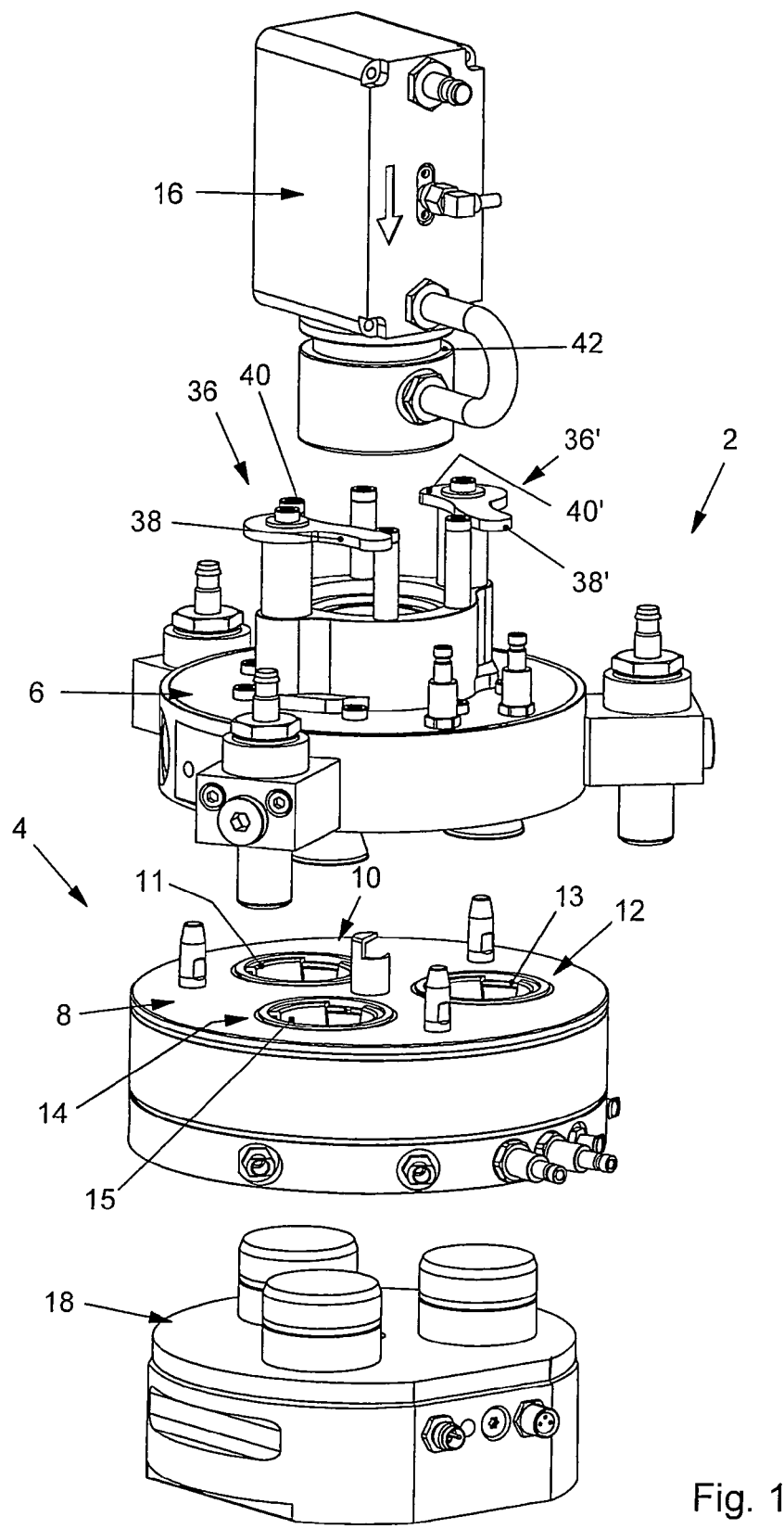
FIG. 1 an exploded view as an explanatory illustration of an embodiment of a device in accordance with the invention, FIG. 2 a view in perspective of the device in accordance with FIG. 1, FIG. 3 a vertical section through the device in accordance with FIG. 2, FIG. 4 a partially sectional view of the device in accordance with FIG. 2, FIG. 5 an exploded view of the sample receptacle module of the device, FIG. 6 a strongly simplified sketch of a top view of the chamber, FIG. 7 a perspective view of a culture/exposure device in accordance with the invention in open position, FIG. 8 a perspective view of an embodiment according to FIG. 7 in closed position, FIG. 9 a vertical section of the embodiment in accordance with FIG. 7 in a detail-reduced illustration; and in FIG. 10 the bottom side of the embodiment according to FIG. 7 in a perspective view.

In FIG. 1, an embodiment of a culture/exposure device is shown being in the following simply referred to as device 2 and being especially suited for cell and/or bacteria cultures. Device 2 is structured in modules and in the embodiment herein shown consists of four modules. The cell and/or bacteria cultures are in a sample receptacle module 8. In the embodiment herein illustrated receptacles 10, 12 and 14 are formed for cultural containers 11, 13 and 15. Under utilization of the device in this embodiment, there are contained cell cultures inside the cultural containers 11, 13 and 15, for example in form of cell culture inserts, which are to be cultivated and exposed to a test atmosphere where necessary.

The sample receptacle module 8 is connected to an aerosol guiding module 6, on which there sits a preparatory module 16.

With the latter, particles contained in the test atmosphere can be charged electrostatically. To effect a fall out of the particles charged electrostatically, a base module 18 can be connected with the sample receptacle module 8.

In addition, locking means 36, 36' are provided, through which, for example, the preparatory module 16 can be locked with the aerosol guiding module 6.

An essential part of the invention lies in the fact that individual modules as a whole can be replaced by modules with other characteristics. In addition, individual modules in their turn may again be structured in a modular manner and can thus be adapted to various requirements. According to the current state of development the existing replacement possibilities, respectively, the own modular structure for the individual modules is described in the following.

Figure 2:
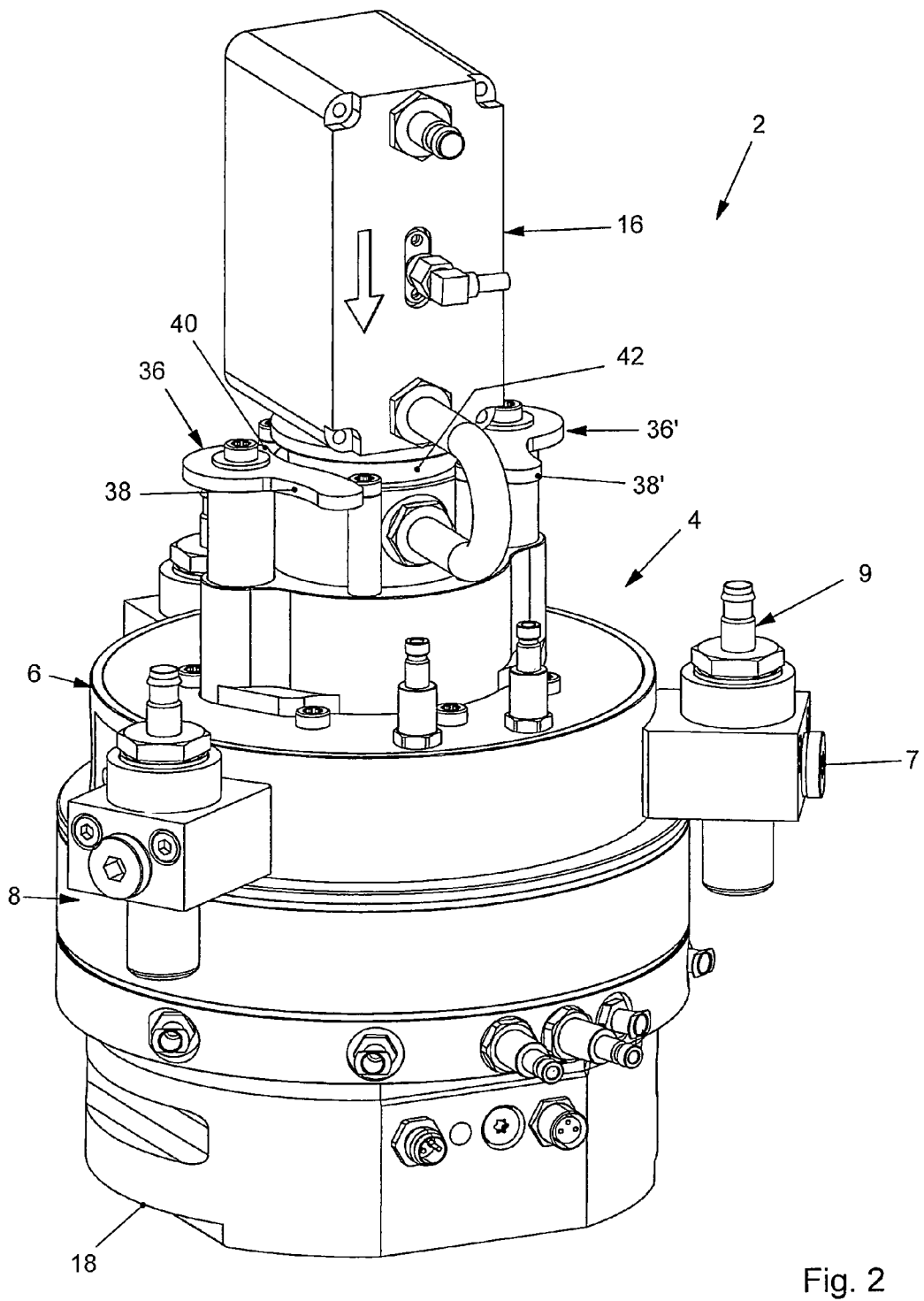

FIG. 2 shows a perspective view of device 2, in which instance the aerosol guiding module 6 is connected with the sample receptacle module 8 as well as the preparatory module 16, and the base module 18 is connected with the sample receptacle module 8.

The preparatory module 16 can, for example, be formed as a charger, in which instance a test atmosphere is charged, for example, in an electrostatic manner. This module could be replaced by a moisturizer, in which the test atmosphere is moisturized, or by a simple inlet adapter, if no pretreatment of the test atmosphere is required.

Figure 3:
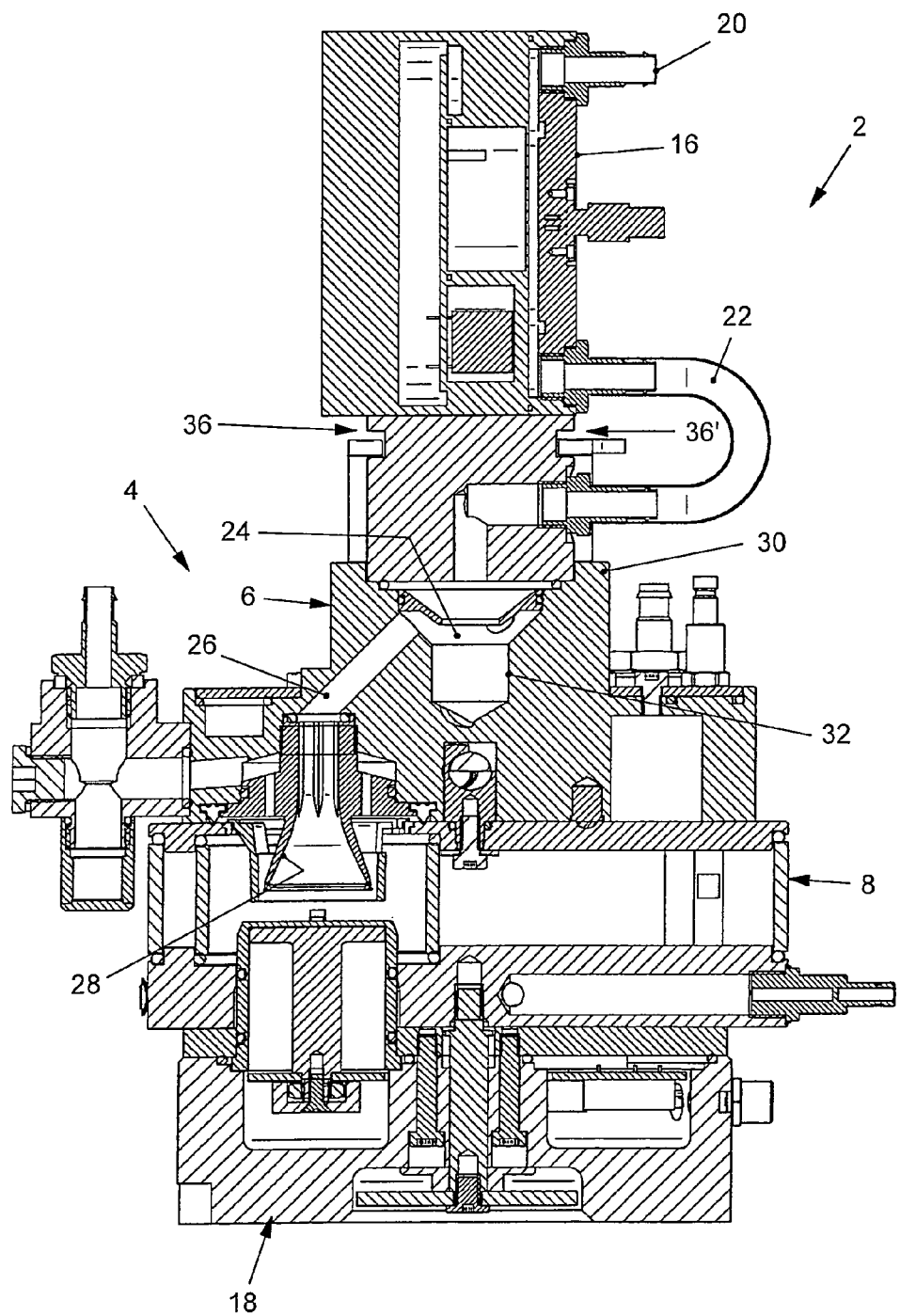

In the embodiment shown in FIG. 3, the preparatory module 16 has an inlet opening 20, via which a test atmosphere, especially a gaseous medium loaded with particles, say smoke, can be led into the device 2.

In order to lead the test atmosphere towards the cultural containers 11, 13, 15, device 2 has a flow guide 22, which leads the gaseous medium from the preparatory module 16 through the aerosol guiding module 6 to a distribution chamber 24. This lies inside a flow passage block 30. From the latter, flow passages of essentially the same length lead to the individual cultural containers. In the embodiment illustrated herein are provided three flow passages, corresponding to the three receptacles 10, 12 and 14 and consequently three cultural containers 11, 13, and 15, of which only one flow passage 26 is visible in section. In the following, only the flow passage 26 is explained in detail. The other two flow passages are structured correspondingly. In the embodiment illustrated in FIG. 4, the flow passages in the direction of the circumference of device 2 are staggered to each other, namely by approximately 120° to each other, corresponding to the arrangement of the receptacles 10, 12 and 14 staggered by approximately 120° to each other. Corresponding to the respective requirements, naturally only two or more than three receptacles and consequently cultural containers 10, 12 and 14, as well as corresponding flow passages 26 can be provided in accordance with the invention.

The flow passage 26 runs from the distribution chamber 24 radially outwards and in a tilted fashion downwards, so that the flow of the test atmosphere also runs radially outwards and in a tilted fashion downwards. In order to improve the flow conditions during the exposure of a culture, a mouth 28 is formed at the end on the output side of the flow passage 26, which broadens in direction of the flow, said mouth being formed as, for example, described in the DE 102 11 324 A1.

Herein, first of all the intra-modular structure of the aerosol guiding module 6 is shown. The mouths 28 belong to replaceable aerosol nozzles which, when desired, can be chosen in correspondence with their length, or with their diameter. Also, sitting in these mouths 28, there may be replaceable grid inserts, which, of course, then can be adapted to the diameter of the aerosol nozzle with or without an orifice.

Belonging to the intra-modular structure of the aerosol guiding module there are, in addition, also the hose adapter 9 or the photometer and openings closed by a sealing plug 7 for insertion of, for example, a temperature sensor or a moisture sensor.

As seen in FIGS. 1 and 3, the sample receptacle module 8 in this embodiment is essentially rotationally symmetric limited, in which instance the receptacles 10, 12 and 14 for the cultural containers are arranged along a circle, which in relation to the rotation symmetric axis is substantially coaxial. In the embodiment illustrated herein, the receptacles 10, 12 and 14 are arranged in equidistance to each other in the direction of the circumference. The three receptacles 10, 12 and 14 are consequently staggered to each other by 120° in the direction of the circumference.

The sample receptacle module 8 as well is structured in an intra-modular manner. This especially applies where the replaceable cultural containers are concerned. It is intended that cell culture inserts of different makes and sizes, or Petri dishes as well can be inserted. To this end, various adapters for the different inserts are provided.

The invention presented herein functions as follows:

When device 2 is in use, the test atmosphere, for example tobacco smoke, flows through the inlet opening 20 into the preparatory module 16, where particles contained in the test atmosphere are charged electrostatically. From the preparatory module 16 the test atmosphere flows into the flow guide 22 and, belonging to the latter, to its distribution chamber 24. From the distribution chamber 24, sub-flows of the test atmosphere flow through the flow passages 26 towards the cultural containers 11, 13 and 15, and impinge the cultures contained in the cultural containers, for example cell or bacteria cultures.

A fall out of the particles contained in the test atmosphere is supported by the circumstance that an electronical field is created in the area of the cultures through a base module 18. Due to the circumstance that the flow path of the test atmosphere from the distribution chamber 24 to each of the individual cultural containers 11, 13 and 15 is of the same length, it is, in accordance with the invention, made sure that the concentration of particles in the test atmosphere is not altered in a varying manner distorting the measurement results because of the flow paths having different lengths.

In the embodiment illustrated herein, only a sub-flow of the test atmosphere is led via the flow passages 26 to the cultural containers 11, 13 and 15. That sub-flow which is not led to the cultural containers 11, 13 and 15 is led away via an axial bore 32 (see FIG. 3) formed in the flow passage block 30 and being in connection with the distribution chamber 24, and via a radial bore 34, being in connection with the bore 32. However, in accordance with the invention it is also possible to lead the total flow of the test atmosphere to the cultural containers 11, 13 and 15.

Figure 4:
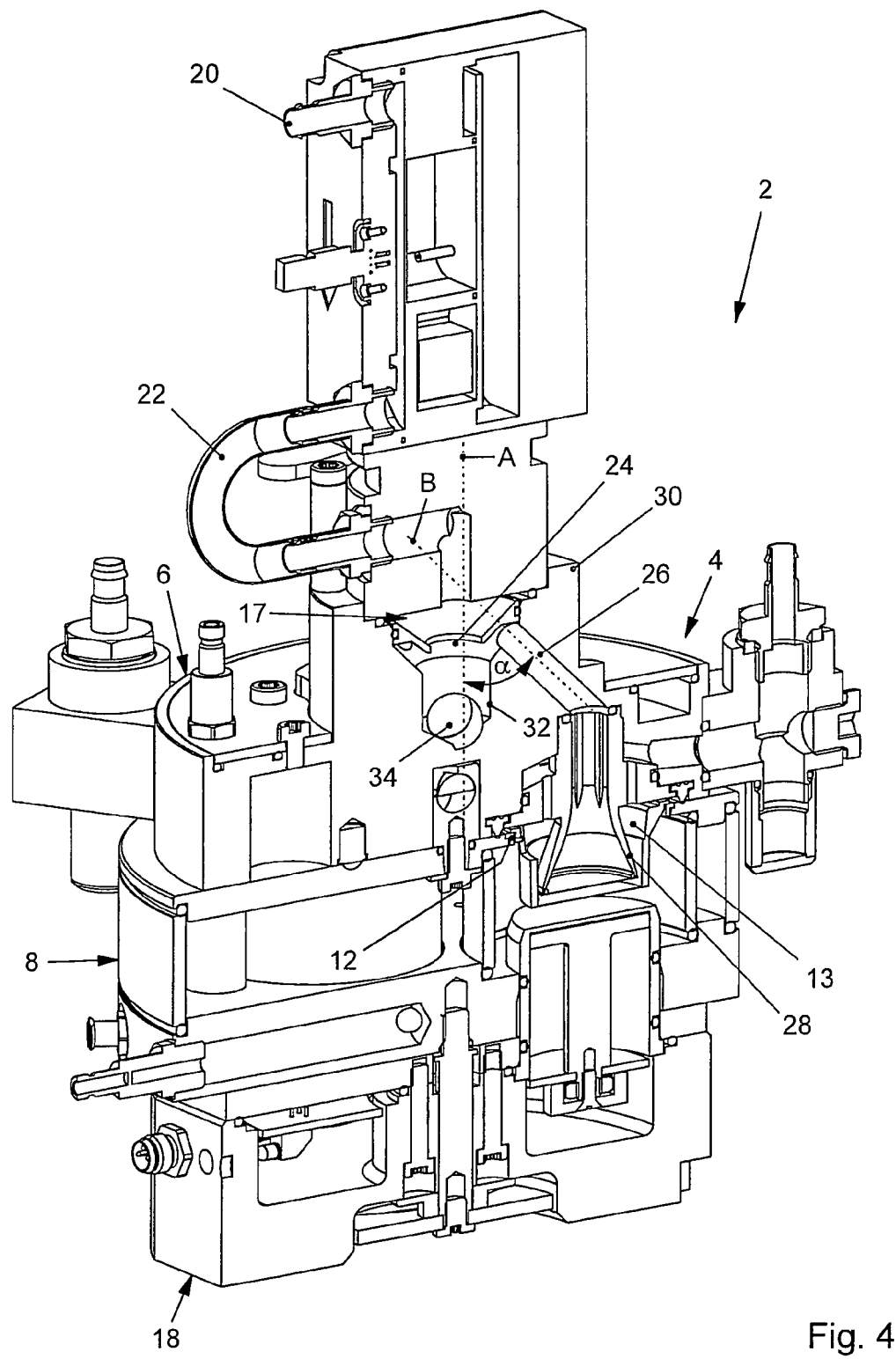

As can be seen in FIG. 4, in the embodiment illustrated herein, a longitudinal axis of the distribution chamber 24 being in this embodiment rotationally symmetric, which longitudinal axis is symbolized by an interrupted line A, proceeds in relation to a longitudinal axis of the flow passage 26, this latter being symbolized by an interrupted line B, under an angle α, this angle being substantially smaller than 90°, namely, in the embodiment illustrated herein approximately 45°. This configuration results in an especially even flow process, undisturbed by abrupt transitions or corners in the flow guide. However this does not apply, if, as shown, a funnel-shaped condensate separator 17 is provided.

After the test atmosphere has streamed over the cell and bacteria cultures contained in the cultural containers 11, 13 and 15, it is let away from the cultural containers 11, 13 and 15. The manner of the latter process of discharging, however, is not of any further interest in the context of the invention and consequently is not explained in any more detail.

In the embodiment illustrated herein, toolless detachable connecting means are provided for connecting the preparatory module 16 with the aerosol guiding module 6. The connecting means have two locking means 36, 36' (see FIG. 1), which is in the following explained in more detail merely referring to locking means 36. The locking means 36' is structured correspondingly. The locking module 36 is mounted to the aerosol guiding module in such a manner that it can be pivoted around a vertical rotation axis, and is formed as a two-armed lever, the one lever arm 38 of which is formed as an actuating arm for turning the locking means 36 around the rotation axis, and the other lever arm 40 of which provides a tight fit with the preparatory module 16. To this end, the preparatory module 16 has a circumferential annular groove 42, into which the lever arm 40 meshes when in connecting position (see FIG. 1). FIG. 1 illustrates the preparatory module 16 in a position in which it is not connected to the aerosol guiding module 6.

To connect the preparatory module 16 with the aerosol guiding module 6, the preparatory module 16 is set on top of the aerosol guiding module 6. Immediately after this step, the locking means 36, 36' are turned around their respective rotation axis, which is a threaded spindle, so that the lever arms 40, 40' mesh with the annular groove 42 and simultaneously press downwards, thus effecting both a tight fit and a traction. The respective threaded spindles of the locking means are correspondingly formed to be left-hand, respectively, right-hand. To loose the preparatory module 16 from the base body 4, the locking modules 36, 36' are turned in such a manner that their lever arms 40, 40' are released from the annular groove 42.

FIG. 2 illustrates the preparatory module 16 in a position in which it is connected with the aerosol guiding module 6. If required to conform with the demands and the desired examinations, the preparatory module 16 can be replaced by another preparatory module in a quick and easy manner, for example, a direct exposure module.

Figure 5:
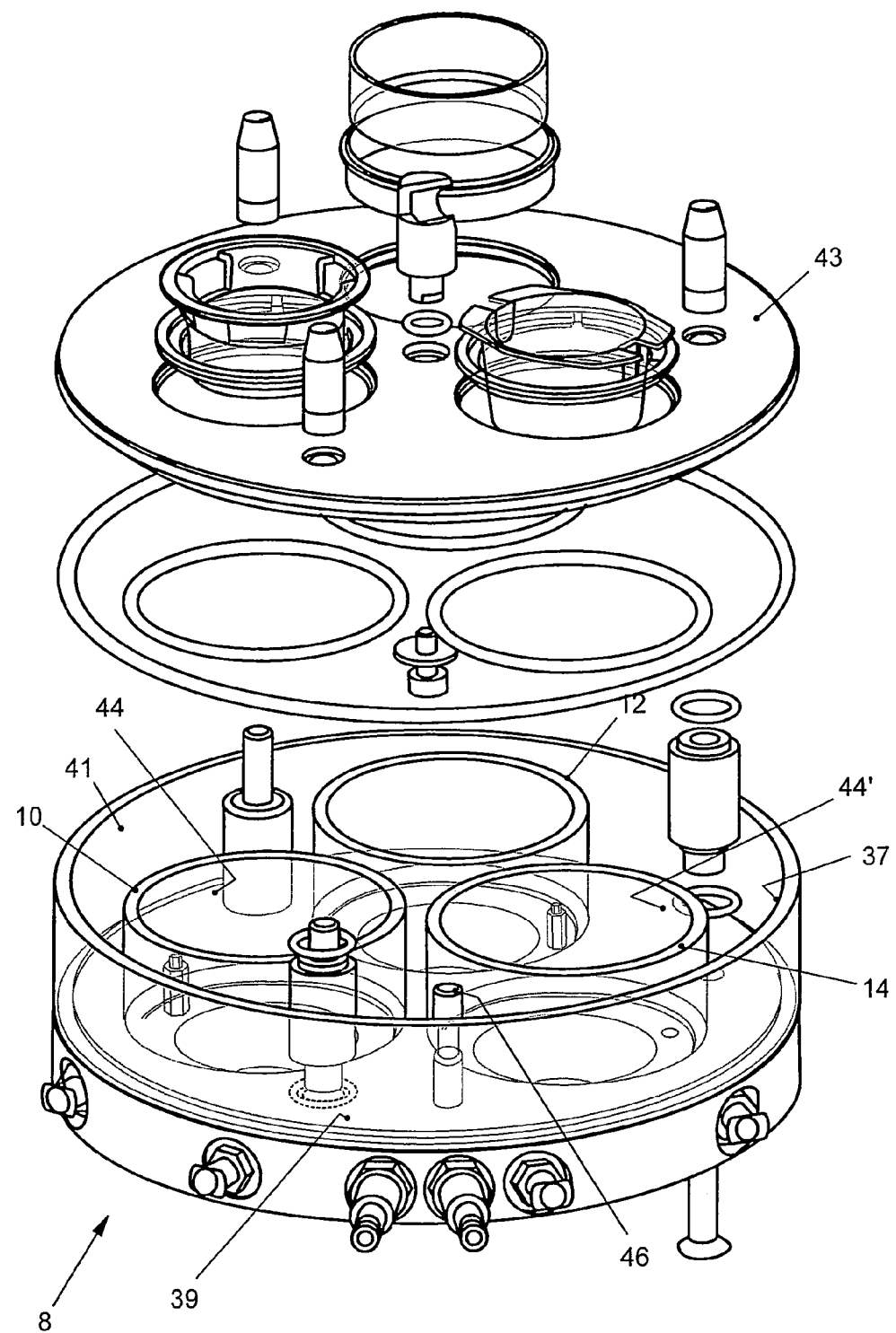

As can be seen in FIG. 5, each of the receptacles 10, 12 and 14 in this embodiment has a limited outer wall and is formed by a glass tube. As can further be seen, a likewise circular limited inner wall 37 is provided being formed by a glass tube as well. Between a bottom 39 of the sample receptacle module, the outer walls of the receptacles 10, 12 and 14, the inner wall 37 and a lid 43 of the sample receptacle module 8, a liquid-tight chamber 41 is provided, which, when the device 2 is in use, is subjected to the through-flow of a temper fluid, the latter taking the form of a temper liquid. The temper liquid enters the chamber 41 by two inlets 44, 44' and exits the chamber 41 by an outlet 46, which in this embodiment is formed as an overflow.

Figure 6:
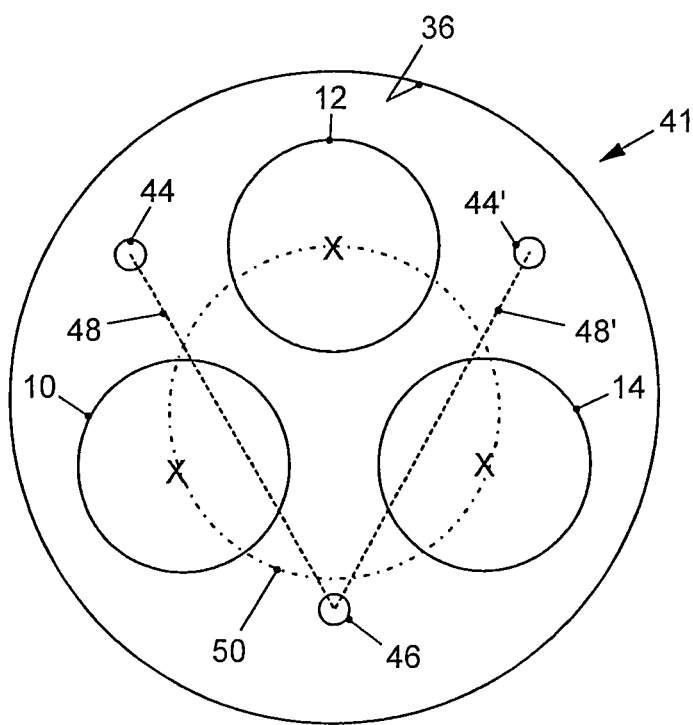

FIG. 6 shows, in a very schematic manner, a top view of the chamber 41, from which is clear that, for example, the receptacle 10 is arranged inside a flow path of the temper liquid running between the inlet 44 and the outlet 46, so that the receptacle 10 is intensely and evenly subjected to the flow of temper liquid. This process results in an especially precise and even tempering of the receptacle 10 and, consequently, of the cultural container 11 received in the receptacle 10. Corresponding circumstances apply for the cultural containers 13 and 15 received in the receptacles 12 and 14. In operating position said containers are, by the way, filled with nutrient solution until a level below the cell cultures and are separated from said solution by a permeable membrane.

As is also seen, the receptacle 10 is arranged on an imaginary connecting line 48 between the inlet 44 and the outlet 46. Corresponding circumstances apply for the receptacle 14, which is arranged on an imaginary line between the inlet 44' and the outlet 46.

In this embodiment, the receptacles 10, 12 and 14 are arranged along the circumference of a circle 50, which is symbolized in FIG. 6 by an interrupted line, said circle 50 being concentric to the substantially circular limited inner wall 37. In the illustrated embodiment the receptacles 10, 12 and 14 are substantially equidistantly arranged to each other in the circumferential direction of the circle 50.

The invention thus allows for a precise and simple tempering of the cultural containers, in order to avoid, for example, condensation. Thus, the study results from examining cell or bacteria cultures are improved by the culture/exposure device in accordance with the invention.

In a further embodiment of the invention in accordance with FIGS. 7 to 10, motion control of the aerosol guiding module 6 in relation to the sample receptacle module 8 is carried out with a guide, which is formed in that two first linear guides 216, 216' vertically guide the aerosol guiding module 6. The first linear guides 216, 216' are each formed by two cylindrical bodies 218, 218', 220, 220', which are telescope-like arranged to each other. To carry out the linear guiding, the respective cylindrical body 218, 218' is connected with the aerosol guiding module 6 and the respective cylindrical body 220, 220' with a holding plate 221.

In as far as the aerosol guiding module 6 is in an open position; the cultural containers 11, 13 and 15 can be removed from the sample receptacle module 8. To this end, the sample receptacle module is led by a second linear guide 222 in a directional movement 224, which is arranged orthogonally in relation to a directional movement 226 of the first linear guide.

Figure 7:
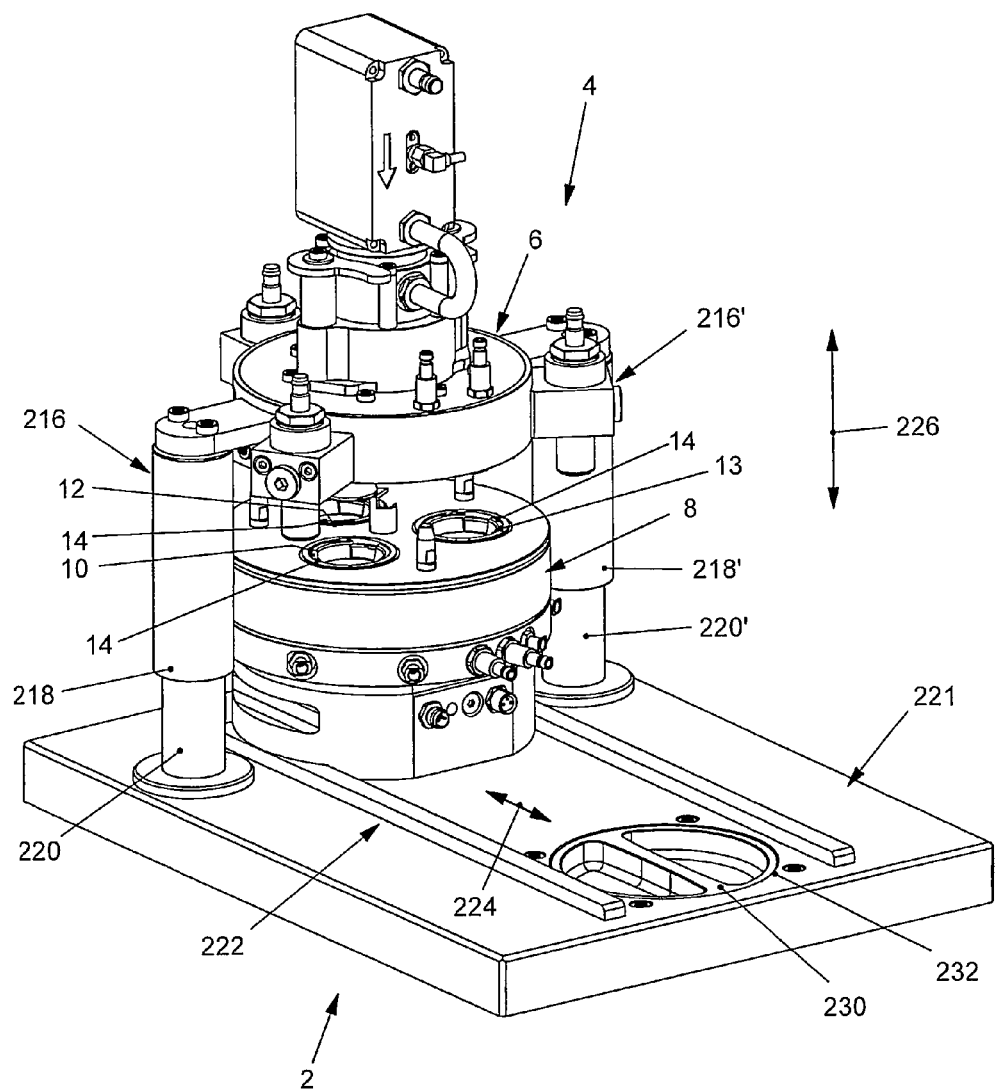
Figure 9:
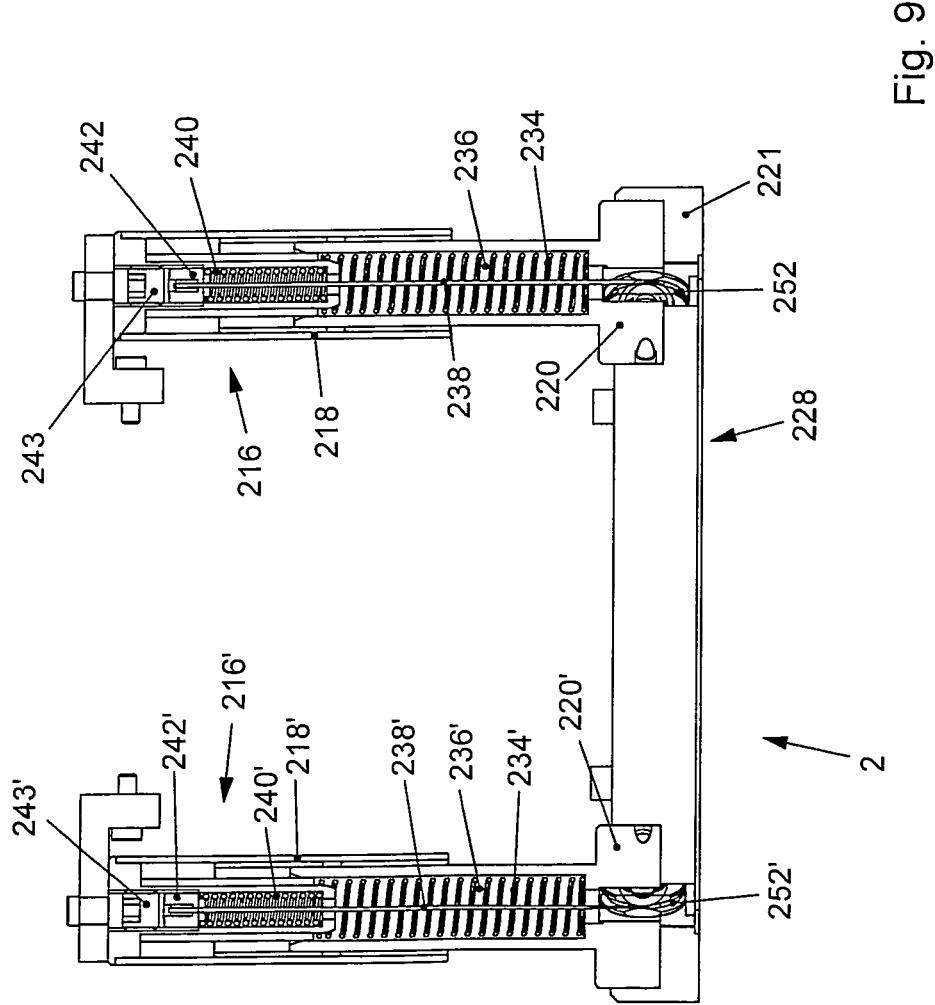
Figure 10:
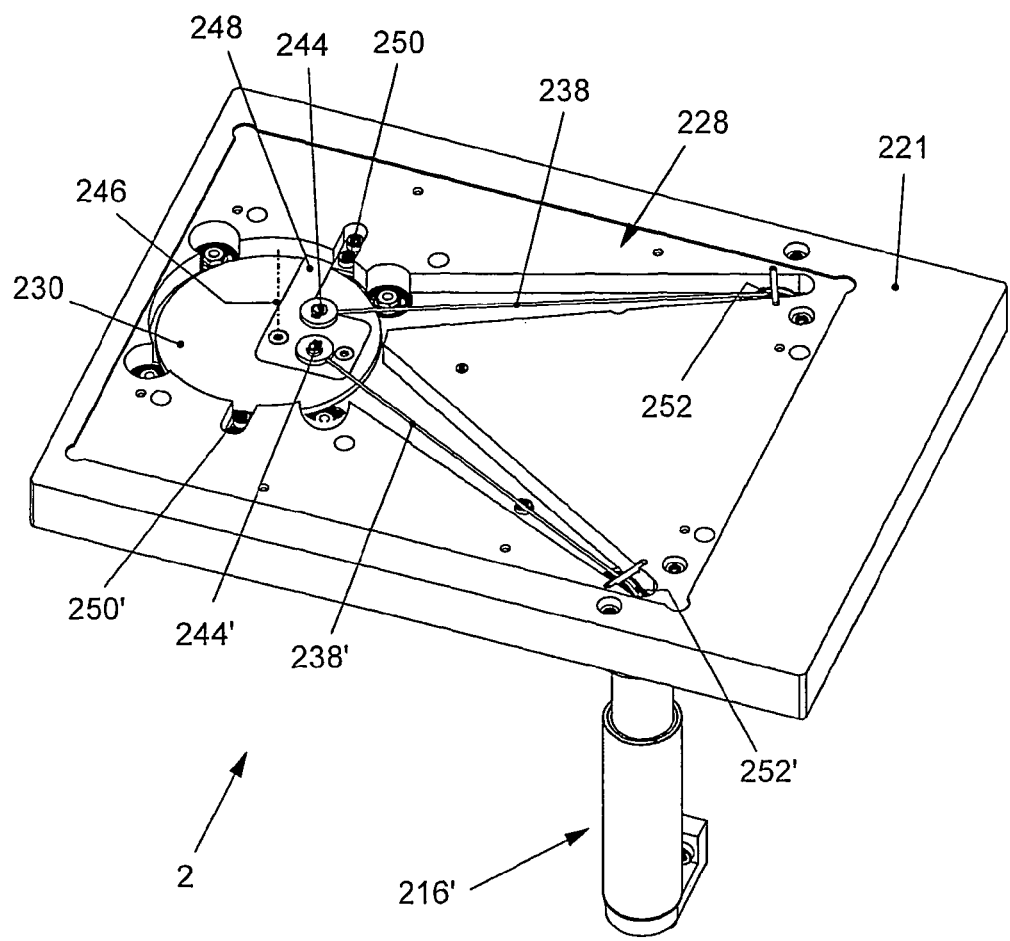

To create a downward movement of the aerosol guiding module 6 via the first linear guide 216, 216', a gear box 228 is positioned at the bottom side of the holding plate 221, which is explained in more detail in FIGS. 7, 9 and 10.

To create an initial movement, the device 2 provides for an actuating means, which is formed by a manually operable rotating disc 230. The manually operable rotating disc 220 is arranged in a recess 232 of the holding plate 221. The kinematic chain between the movement of the rotating disc 230 and the first linear guide 216, 216' is explained in greater detail in the following.

The use of a rotating disc 230 in combination with the gear box 228 has the advantage that the ratio between the force at wire ropes 238, 238' (see FIG. 9) and the torque of the rotating disc 230 is proportional to 1/sin(rotary angle of the rotating disc 230), so that, especially shortly before the end of the operation of the rotating disc 230 (180°. closed position) very high cord forces can be produced, which is useful, since in this position the sealing between the aerosol guiding module and the sample receptacle module need to be pre-stressed.

Figure 8:
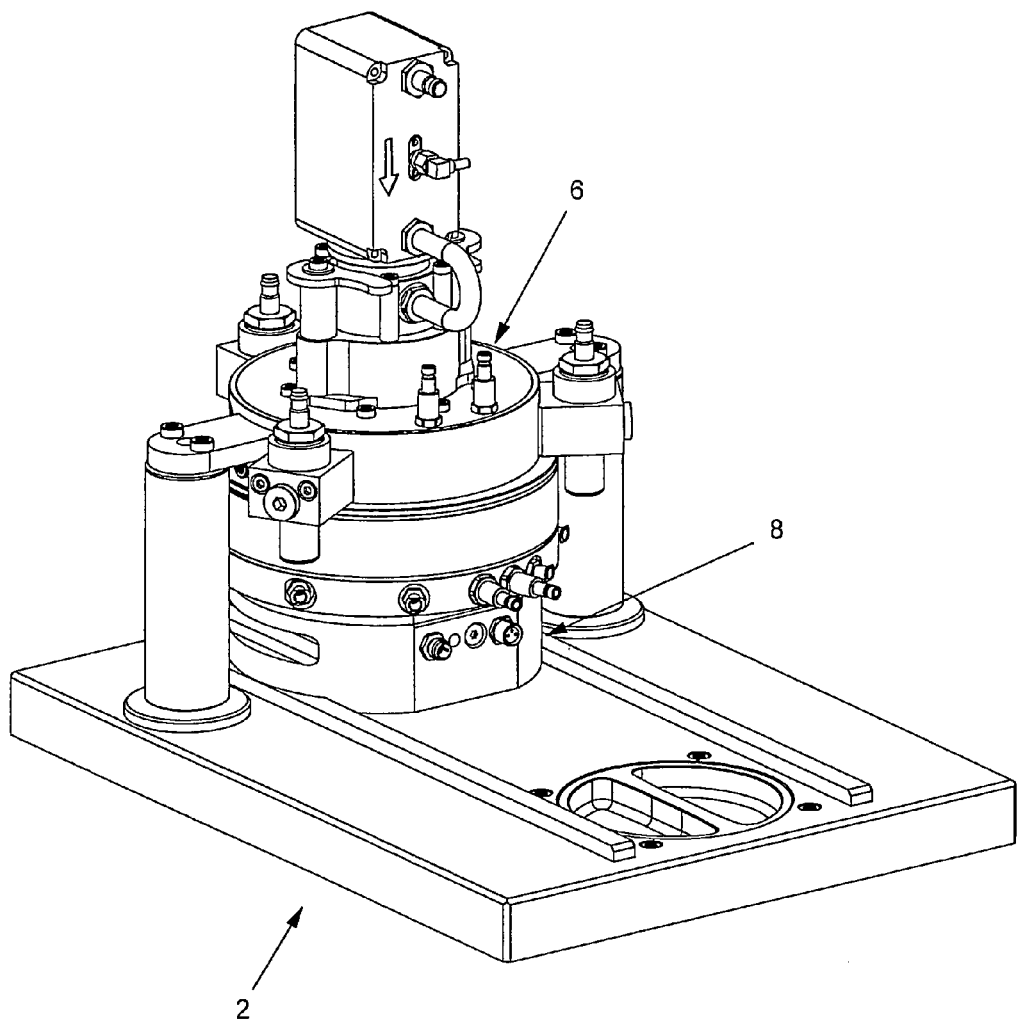

FIG. 8 shows the embodiment of device 2 in a closed position, which is reached after the aerosol guiding module 6 has been moved in a downward movement in relation to the sample receptacle module 8. In the closed position, the aerosol guiding module is thus, in terms of flow, connected to the sample receptacle module 8.

FIG. 9 shows the embodiment of device 2 in a vertical section according to FIG. 7, in which instance the illustration is reduced to the details essential for understanding.

For the automatic movement of the aerosol guiding module 6 (see FIG. 7) into the open position, the first linear guide 216, 216' has a spring 234, 234', which is formed as a spiral spring and which is in the closed position of the aerosol guiding module tensed, so that its tension force is transformed into kinetic energy of the aerosol guiding module 6 in order to reach the open position.

The spring 234, 234' is arranged in the interior 236, 236' of the cylindrical body 220 such that it is tensioned when the cylindrical body 218 descends. This circumstance results in the tension force supporting the movement needed to reach the open position.

On the cylindrical body 218, 218' a wire cord 238, 238' is arranged, by which an initial movement is transmitted in a drive movement for the first linear guide 216, 216'. The transformation of the movement of the wire cord 238, 238' occurs via the gear box 228, so that the initial movement, which occurs via the rotating disc 230, is transformed into a drive movement for the first linear guides 216, 216'.

To tense the respective wire cord 238, 238', a respective additional spring 240, 240' is provided, which is arranged in the interior of the cylindrical body 218, 218'. Said spring also serves to compensate possible undesired changes in length of the respective wire cord 238, 238'. The fixing of the wire cord 238, 238' is done via a holding body 242, 242', which is arranged at the respective additional spring 240, 240'.

The holding bodies 242, 242' are arranged at adjusting screws 243, 243', which in their turn allow for adjusting the pre-stressing of the springs 240, 240' under synchronic preliminary setting and on the other hand allow for compensating a difference in length between the wire cords 238, 238', given opposed preliminary setting.

FIG. 10 shows the culture/exposure device in a perspective view from below. A part of the gear box 228 is arranged at the bottom side of the holding plate 221. For the transformation of movement, two wire cords 238, 238' are arranged at the manually operable rotating disc 230 by means of a respective fixing point 244, 244', of which in each case a wire cord is correlated with the first linear guide 216, 216'. By turning the rotating disc 230, the fixing points 244, 244' perform a circular movement around a rotation axis 246 of the rotating disc 230, whereby the respective distance from the fixing point 244, 244' to a guiding role 252, 252' is shortened. Due to the constant, or at least almost constant, length of the wire cords 238, 238' the change in distance is transformed into a downward or a lifting movement of the first linear guide 216, 216'. This results in a pivotal movement of the rotating disc 230 causing a lifting or sinking of the aerosol guiding module 6. To guide the movement, the rotating disc 230 has a stop 248, which, due to counter-stops 250, 250' arranged on the holding plate 221, limits the movement of the fixing points 244, 244', whereby the movement of the first linear guides 216, 216' as well and consequently the lifting movement of the aerosol guiding module is limited.

A further limitation of the movement of the fixing points 244, 244' is achieved by the arrangement of the fixing points 244, 244' on the rotating disc 230. These are arranged on the rotating disc 230 in such a manner that, when reaching the open position, or the closed position, dead point positions result, which prevent an automatic movement of the rotating disc 230, so that a movement of the aerosol guiding module 6 out of open position, or out of closed position is only possible if the rotating disc 230 is operated.

In this context, the additional spring 240, 240', besides fulfilling the objective already stated, also the following objects:

To make sure that the rotating disc 230 does not move out of the dead point positions when this is not desired, the rotating disc 230, in order to hold the closed position, is turned to a point exceeding the dead point position, whereby in combination with the stop 248 and the counter stops 244, 244' it is achieved that the rotating disc 230 cannot turn backwards automatically. However the result is that the aerosol guiding module 6 on the other hand can move in the direction of the open position, whereby the sealing (not illustrated) between the aerosol guiding module 6 and the sample receptacle module 8 relaxes and a big gap between the aerosol guiding module 6 and the sample receptacle module 8 is possibly formed. To prevent a too large gap, which would possibly weaken the sealing effect, or cancel it, the additional spring 240, 240' serves to prevent, or diminish, an undesired movement of the aerosol guiding module 6 in direction of the open position.

The additional spring 240, 240' also compensates tolerances, which would otherwise have to be redressed in order to secure a fluid technical connection between the aerosol guiding module 6 and the sample receptacle module 8.

To guide and transform the direction of movement of the wire cord 238, 238', the gear box 228 has the respective guiding roles 252, 252' (see FIG. 9). Due to this circumstance, the pivotal movement of the rotating disc 230 is transformed into a linear movement for moving the aerosol guiding module 6, so that under the effect of the first linear guide 216, 216', the aerosol guiding module 6 can perform a downward movement. The lifting movement occurs, as already described, after canceling the corresponding dead point position by means of an initial turning of the rotating disc 230.

The invention claimed is:

1. A culture/exposure device for cell and bacteria cultures comprising:
 a plurality of modules including a base module, a sample receiving module on the base module, an aerosol guide module on the sample receptacle module and a preparation module on the aerosol guide module, wherein each of said plurality of modules are adapted to be selectively connected to one another, detachable from one another and exchangeable with one another;
 the sample receiving module having a plurality of receptacles, wherein each of said plurality of receptacles is adapted to receive an individual cultural container;
 the preparation module having an inlet and a flow guide wherein one end of said inlet is connected to a test atmosphere and another end connected to said flow guide which leads gaseous medium from the preparation module to the aerosol guide module;
 the aerosol guide module having a distribution chamber connected to said flow guide, wherein said distribution chamber has a plurality of flow passages wherein each of the flow passages communicates the test atmosphere to an individual cultural container for charging each cultural container in the plurality of receptacles, the plurality of flow passages are the same length so as to insure that the concentration of particles in the test atmosphere is not altered in a varying manner thus distorting measurement results.

2. The culture/exposure device according to claim 1, wherein each of the receptacles is arranged in a chamber through which a temperature-controlling fluid flows, an inlet is provided in the sample receiving module for feeding the temperature-controlling fluid and an outlet in the sample receiving module is provided for removing the temperature-controlling fluid, wherein a flow path for the temperature-controlling fluid is formed, and each receptacle is arranged in the flow path such that the culture container forms a flow obstacle for the temperature-controlling fluid, and each chamber has a substantially circularly demarcated inner wall.

3. The culture/exposure device according to claim 1, wherein releasable locking devices are provided for connecting the preparation module to the aerosol guide module, wherein the locking devices are adapted to be released without the need of a tool.

4. The culture/exposure device according to claim 3, wherein the locking devices provide a positive locking between the preparation module and the aerosol guide module.

5. The culture/exposure device according to claim 1, wherein the preparation module is constructed as a module for electrostatic charging of particles contained in the test atmosphere.

6. The culture/exposure device according to claim 1, wherein the base module is connected detachably to the sample-receiving module, the base module is configured for application of an electrostatic field.

7. The culture/exposure device according to claim 1, wherein the aerosol guide module and the sample-receiving module are guided on a guide relative to one another and can be moved by a drive device relative to one another between a closed position wherein the flow guide is connected for flow to the culture container and an open position wherein the flow guide is closed for flow from the culture container.

8. The culture/exposure device according to claim 7, wherein the guide comprises at least a first linear guide for linear guiding of the aerosol guide module and of the sample-receiving module relative to one another between the closed position and the open position.

9. The culture/exposure device according to claim 8, wherein the guide comprises a second linear guide for linear guiding of the sample-receiving module orthogonally or substantially orthogonally to the guiding direction of the first linear guide for horizontal or substantially horizontal guiding of the sample-receiving module.

10. The culture/exposure device according to claim 7, wherein the drive device comprises at least one gearing mechanism for conversion of an input movement into a drive movement for relative movement of the aerosol guide module with respect to the sample-receiving module and for conversion of an input movement into a drive movement for relative movement of the sample-receiving module with respect to the aerosol guide module.

11. The culture/exposure device according to claim 10, wherein the gearing mechanism comprises at least one of cable-, belt- or chain-like traction means for transmission of the input movement as a drive movement for relative movement of the aerosol guide module with respect to the sample-receiving module and for relative movement of the sample-receiving module with respect to the aerosol guide module.

12. The culture/exposure device according to claim 10, wherein the gearing mechanism converts the input movement into a lowering movement of the aerosol guide module with respect to the sample-receiving module for a vertical or substantially vertical lowering movement.

\* \* \* \* \*